(12) United States Patent
Baba

(10) Patent No.: US 7,796,342 B2
(45) Date of Patent: Sep. 14, 2010

(54) IMAGING LENS SYSTEM AND CAPSULE ENDOSCOPE

(75) Inventor: Tomoyuki Baba, Saitama (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/327,516

(22) Filed: Dec. 3, 2008

(65) Prior Publication Data
US 2009/0141364 A1 Jun. 4, 2009

(30) Foreign Application Priority Data

| Dec. 4, 2007 | (JP) | ............... P2007-313692 |
| Dec. 4, 2007 | (JP) | ............... P2007-313693 |
| Dec. 4, 2007 | (JP) | ............... P2007-313694 |

(51) Int. Cl.
*G02B 3/00* (2006.01)
*A61B 1/00* (2006.01)
(52) U.S. Cl. .................. 359/648; 359/725; 600/101
(58) Field of Classification Search ......... 359/648–651; 600/101, 129, 130, 160, 173, 176
See application file for complete search history.

(56) References Cited

U.S. PATENT DOCUMENTS 6,801,370 B2 * 10/2004 Sekiyama et al. ........... 359/726

| 2005/0054901 | A1 | 3/2005 | Yoshino |
| 2005/0054902 | A1 | 3/2005 | Konno |
| 2005/0124858 | A1 | 6/2005 | Matsuzawa et al. |
| 2007/0055105 | A1 * | 3/2007 | Matsuzawa et al. ......... 600/176 |
| 2008/0146877 | A1 | 6/2008 | Matsuzawa et al. |

FOREIGN PATENT DOCUMENTS

| JP | 2005-080789 A | 3/2005 |
| JP | 2005-080790 A | 3/2005 |
| JP | 2006-061438 A | 3/2006 |

* cited by examiner

*Primary Examiner*—Darryl J Collins
(74) *Attorney, Agent, or Firm*—Birch, Stewart, Kolasch & Birch, LLP

(57) ABSTRACT

A capsule endoscope has an imaging lens system that forms an image of a substantially spherical object in a plane shape on the imaging surface. The imaging lens system includes first to fourth lenses and an aperture diaphragm. The surface shapes and arrangement thereof are set in consideration of a front cover of the capsule endoscope and a cover glass of an imaging device. Further, the imaging lens system is configured so that the following conditional expression is satisfied with respect to an arbitrary half angle of view $\omega$:

$$0.7 < (Y(\omega+\Delta\omega) - Y(\omega))/Y(\Delta\omega)$$

where $Y(\omega)$ denotes an image height for the half angle of view $\omega$ of the imaging lens system, and $\Delta\omega$ denotes an amount of minute change of the half angle of view ($\omega$).

20 Claims, 14 Drawing Sheets

IMAGING LENS SYSTEM AND CAPSULE ENDOSCOPE

CROSS-REFERENCE TO RELATED APPLICATIONS

This application is based upon and claims the benefit of priority from the Japanese Patent Application Nos. 2007-313692, 2007-313693 and 2007-313694 all of which were filed on Dec. 4, 2007; the entire contents of which are incorporated herein by reference.

BACKGROUND OF THE INVENTION

1. Technical Field

The invention relates to an imaging lens system for use in an endoscope for examining the interior of the body, and more specifically, to an imaging lens system for use in a capsule type endoscope that is used in a manner that a patient swallows it.

2. Related Art

Diagnosis using an endoscope has been actively performed in the medical field. The diagnosis using an endoscope is performed by inserting, into the patient's body, a flexible insertion portion which is configured so that the flexible insertion portion can be operated freely to bend in a desirable direction. A small-size imaging portion including an illuminator, a imaging lens system, and an imaging device is provided at the end of the insertion portion. Therefore, the insertion type endoscope is arbitrarily changed within a predetermined range in the patient's body by the doctor's operation, and can accurately image a part which is suspected as being a lesion, which helps accurate medical diagnosis such as correct diagnosis and early detection of lesions.

Although the shape of the insertion-type endoscope is designed so as to reduce the load on the patient at the time of insertion, the insertion of the long insertion portion into the body is a heavy load on the patient. There may be cases where anesthesia or the like is necessary when the insertion-type endoscope is used.

In recent years, to further reduce the load on the patient, a so-called capsule type endoscope (hereinafter, may be referred to as a "capsule endoscope") in which a small-size imaging apparatus is accommodated in a swallowable capsule has been being developed and is putting to practical use. Since this capsule endoscope is formed in an easily swallowable size, the load on the patient is significantly light as compared with the insertion-type endoscope. However, it is difficult to control its position and its direction inside the body.

Therefore, in order to take images of lesions without missing any even when the posture of the capsule endoscope inside the body is not desirable, it is desirable that the capsule endoscope be provided with a wide-angle imaging lens system so that an image of as wide area as possible can be taken.

From the above circumstances, a capsule endoscope has been known in which the capsule size is reduced while a wide imaging area is secured (see JP 2005-80789 A (corresponding to US 2005/0054902 A)). The following are also known: a capsule endoscope that attains not only a smaller size and a wider angle but also, for example, an optimum depth of field (see JP 2005-80790 A (corresponding to US 2005/0054901 A)); and a capsule endoscope that excellently illuminates a cylindrical structure (see JP 2006-61438 A (corresponding to US 2005/0124858 A, US 2007/0055105 A, and US 2008/0146877 A)).

It is important for the capsule endoscope to be easy to swallow. Therefore, in order to minimize its size, the capsule endoscope of the related art is provided with a lens including a minimum number of lenses, for example, a two-group, two-lens wide-angle lens as an imaging lens system.

Although it is desirable that the capsule endoscope be provided with a wide-angle imaging lens system as described above, more conspicuous distortion occurs as an imaging lens system has a wider angle of view like the other types of imaging lens systems. For example, as is often seen in wide-angle lenses, if a barrel-shaped distortion is caused, not only an obtained image is distorted but also the obtained image becomes small in the peripheral part of the obtained image.

Images taken by the capsule endoscope are images of the interior of the human body, and are images used for determining whether a lesion is present or absent. However, a lesion size differs according to a type and/or a degree of progression. In many cases, lesions are extremely small. Therefore, if such a small lesion is present in the peripheral part of the obtained image where a barrel-shaped distortion occurs as described above, the lesion would be smaller than its actual size and might be overlooked.

On the other hand, it is important for the capsule endoscope to be easy to swallow, and the capsule endoscope is used only once and then thrown away. Therefore, for price reduction and size reduction, the capsule endoscope is provided with a lens having a minimum number of lenses, for example, a two-group, two-lens wide-angle lens as its imaging lens system. There is no conventional imaging lens system for the capsule endoscope in which distortion is improved. Thus, an imaging lens system is demanded in which distortion is improved while its capsule size is kept small.

SUMMARY OF THE INVENTION

The invention has been made in view of the above circumstances, and provides a wide-angle imaging lens system in which distortion is improved while an easy-to-swallow size is kept, and a capsule endoscope that is provided with the imaging lens system and prevents a lesion from being overlooked in the entire imaging area.

According to an aspect of the invention, an imaging lens system for a capsule endoscope is configured to be disposed in a dome-shaped transparent cover. When a spherical object is imaged, the imaging lens system forms an image of an entire area from a center of the object to a maximum angle of view in a substantially same plane. The following conditional expression is satisfied with respect to an arbitrary half angle of view ω:

$$0.7 < (Y(\omega + \Delta\omega) - Y(\omega))/Y(\Delta\omega)$$

where $Y(\omega)$ denotes an image height for the half angle of view ω of the imaging lens system, and $\Delta\omega$ denotes an amount of minute change of the half angle of view (ω).

Also, the following conditional expression may be satisfied:

$$2\omega_{MAX} > 135 \text{ degrees}$$

where $\omega_{MAX}$ denotes a maximum half angle of view.

According to another aspect of the invention, a capsule endoscope includes the imaging lens system described above.

With the above-described configuration, the following can be provided: a wide-angle imaging lens system in which distortion is improved while an easy-to-swallow size is kept;

and a capsule endoscope that is provided with the imaging lens system and prevents a lesion from being overlooked in the entire imaging area.

According to further another aspect of the invention, an imaging lens system for a capsule endoscope is configured to be disposed in a dome-shaped transparent cover. The imaging lens system includes four lenses. When a spherical object is imaged, the imaging lens system forms an image of an entire area from a center of the object to a maximum angle of view in a substantially same plane.

The imaging lens system may include, in order from an object side, a first lens group having a negative refractive power, a stop, and a second lens group having a positive refractive power.

The following conditional expression may be satisfied:

$$2\omega_{MAX} > 135 \text{ degrees}$$

where $\omega_{MAX}$ denotes a maximum half angle of view.

According to still another aspect of the invention, a capsule endoscope includes the imaging lens system described above.

With the above-described configuration, a capsule endoscope can be provided that has a wide-angle lens in which distortion is improved while an easy-to-swallow size is kept and prevents a lesion from being overlooked in the entire imaging area.

According to still further another aspect of the invention, an imaging lens system for a capsule endoscope is configured to be disposed in a dome-shaped transparent cover. The imaging lens system includes five lenses. When a spherical object is imaged, the imaging lens system forms an image of an entire area from a center of the object to a maximum angle of view in a substantially same plane.

The imaging lens system may include, in order from an object side, a first lens group having a negative refractive power, a stop, and a second lens group having a positive refractive power.

The following conditional expression may be satisfied:

$$2\omega_{MAX} > 135 \text{ degrees}$$

where $\omega_{MAX}$ denotes a maximum half angle of view.

According to still further another aspect of the invention, a capsule endoscope includes the imaging lens system described above.

With the above-described configuration, the following can be provided: a wide-angle imaging lens system in which distortion is improved while an easy-to-swallow size is kept; and a capsule endoscope that is provided with the imaging lens system and prevents a lesion from being overlooked in the entire imaging area.

DETAILED DESCRIPTION OF EMBODIMENTS OF THE INVENTION

Figure 1:
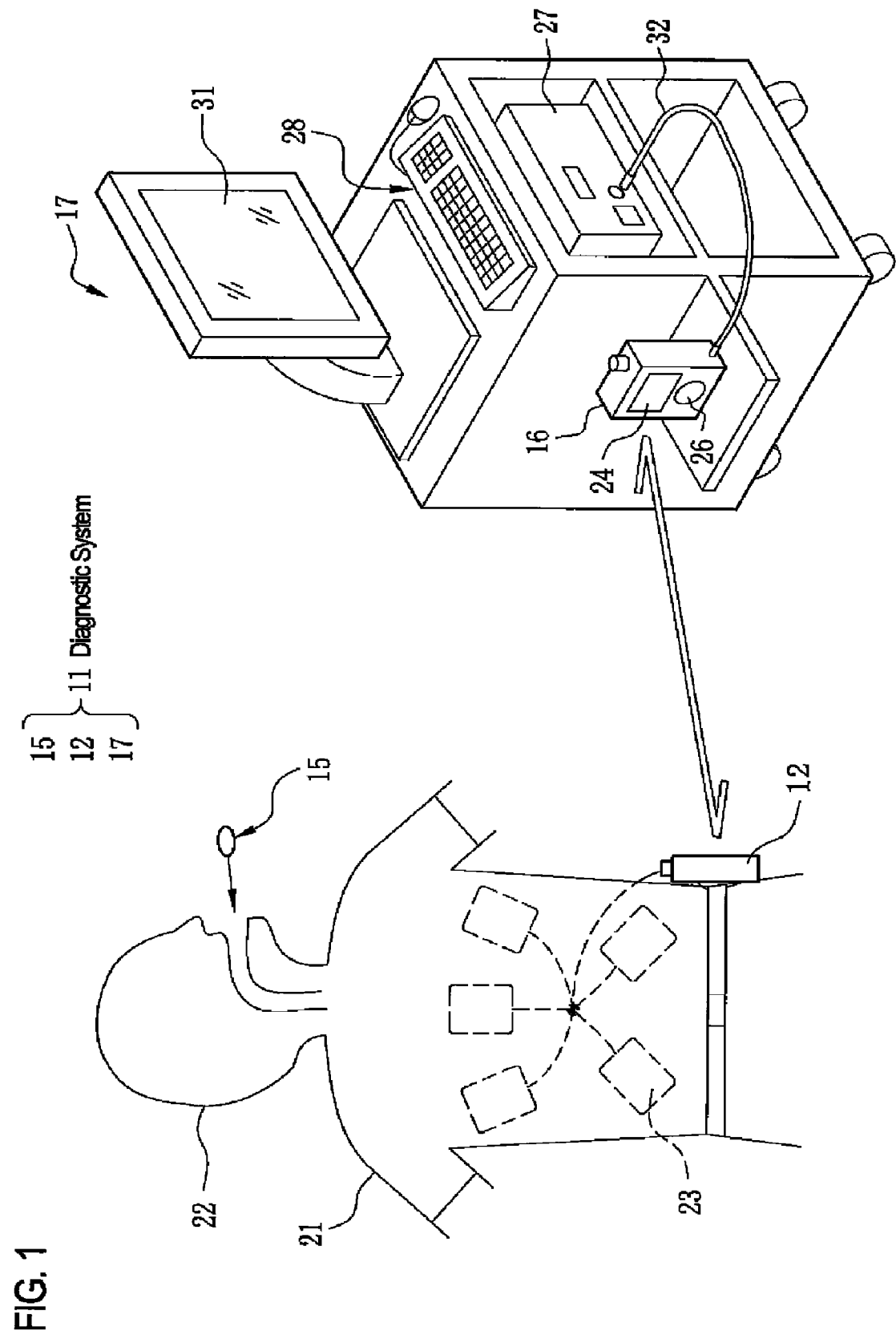
FIG. 1 is an explanatory view showing the general outline of a diagnostic system using a capsule endoscope.

As shown in FIG. 1, a capsule endoscope diagnostic system 11 includes a capsule endoscope 15, a receiver 16, and a workstation 17.

The capsule endoscope 15 is used by being swallowed into the body from the mouth of a patient 22 wearing a shielding shirt 21. When passing through the intra-body passageway, the capsule endoscope 15 takes images of the inner wall thereof. The image data taken by the capsule endoscope 15 is wirelessly transmitted to the receiver 16. This image data communication is performed through a transmission antenna provided in the capsule endoscope 15 and a reception antenna 23 provided in the shielding shirt 21.

The receiver 16 has an LCD 24 that displays various setting screens and an operation portion 26 for performing various setting operations. At the time of the examination when the capsule endoscope 15 is inside the body of the patient 22, the receiver 16 is carried by the patient 22, and receives and stores the image data that is wirelessly transmitted from the capsule endoscope 15 as described above. When diagnosis is performed based on the obtained image data, the receiver 16 is connected to the workstation 17 for diagnosis, and the stored image data is read out.

The workstation 17 includes a processor 27, an operation portion 28 including a keyboard and a mouse, and a display 31. The processor 27 is connected to the receiver 16, for example, via a USB cable 32, and obtains the image data stored in the receiver 16. Also, the image data acquired by the processor 27 in this way is stored and managed for each patient. When diagnosis is performed based on the image data obtained by the capsule endoscope 15, the workstation 17 generates a television image from the stored image data based on the operation by the operation portion 28, and displays it on the display 31.

Figure 2:
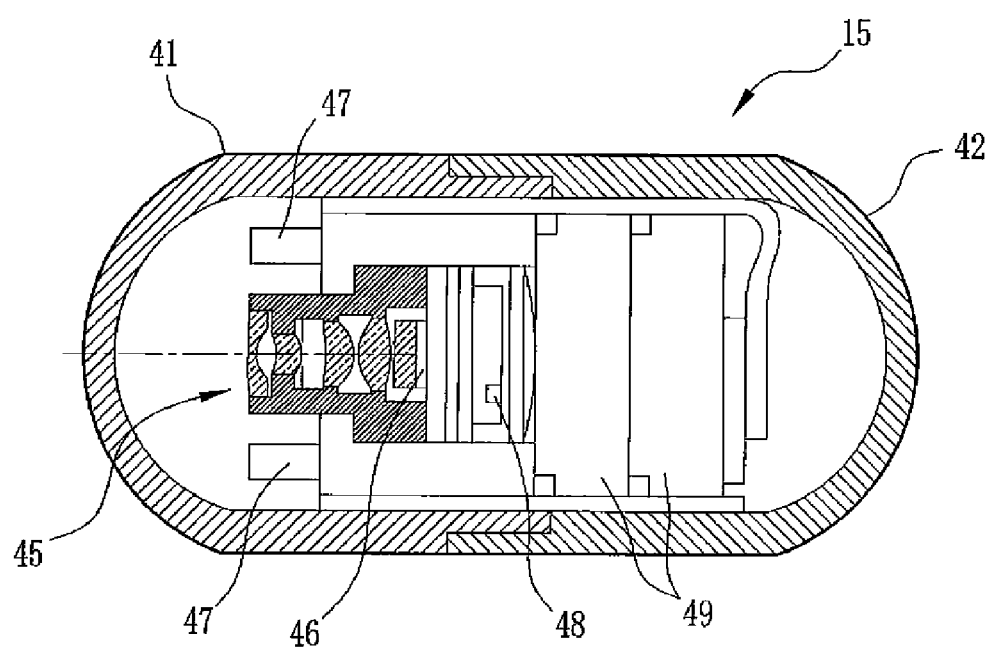
FIG. 2 is a section view showing the configuration of the capsule endoscope.

As shown in FIG. 2, the outside shape of the capsule endoscope 15 is formed by a front cover 41 and a rear cover 42. The front cover 41 has its front surface formed in a dome shape, and engages with the rear cover 42 to form a cylindrical watertight space whose end surfaces are dome-shaped. At least the front surface of the front cover 41 is made of a transparent material, and transmits light from the interior of the body of the patient 22 which is an object (hereinafter, referred to merely as an "object").

An imaging lens system 45, an imaging device 46, illumination devices 47, a transmission antenna 48, and button cells 49 are accommodated in the space formed by the front cover 41 and the rear cover 42. That is, the components such as the imaging lens system 45 are watertightly covered by the front cover 41 and the rear cover 42.

The illumination devices 47 are optical systems that uniformly illuminate the object, for example, by a white LED. The plurality of illumination devices 47 are provided around the imaging lens system 45. The imaging lens system 45 forms an image on the imaging device 46 according to light from the object. The imaging lens system 45 is a wide-angle lens including four to five lenses and an aperture diaphragm. The imaging device 46 is, for example, a CCD-type imaging device, and generates image data by photoelectrically converting the image of the object formed on the imaging surface by the imaging lens system 45.

The transmission antenna 48 transmits the image data generated by the imaging device 46 to the above-described receiver 16 at any time. The button cells 49 supply power to the illumination devices 47, the imaging device 46, the transmission antenna 48, and the like at the time of examination when the capsule endoscope 15 is in the body of the patient 22. Such power supply is performed by a power supply circuit.

Figure 3:
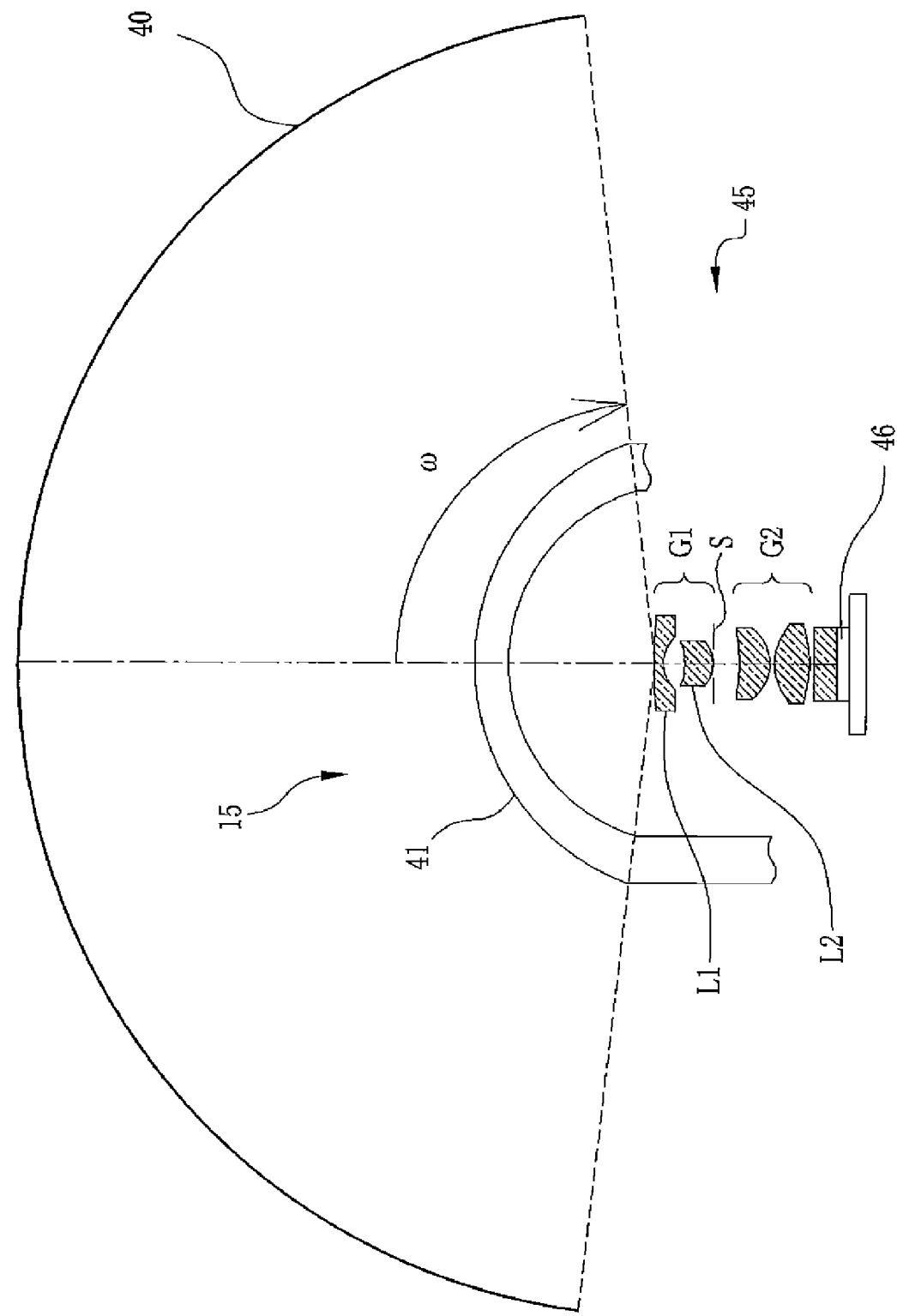
FIG. 3 is an explanatory view showing an imaging area of the capsule endoscope.
Figure 4:
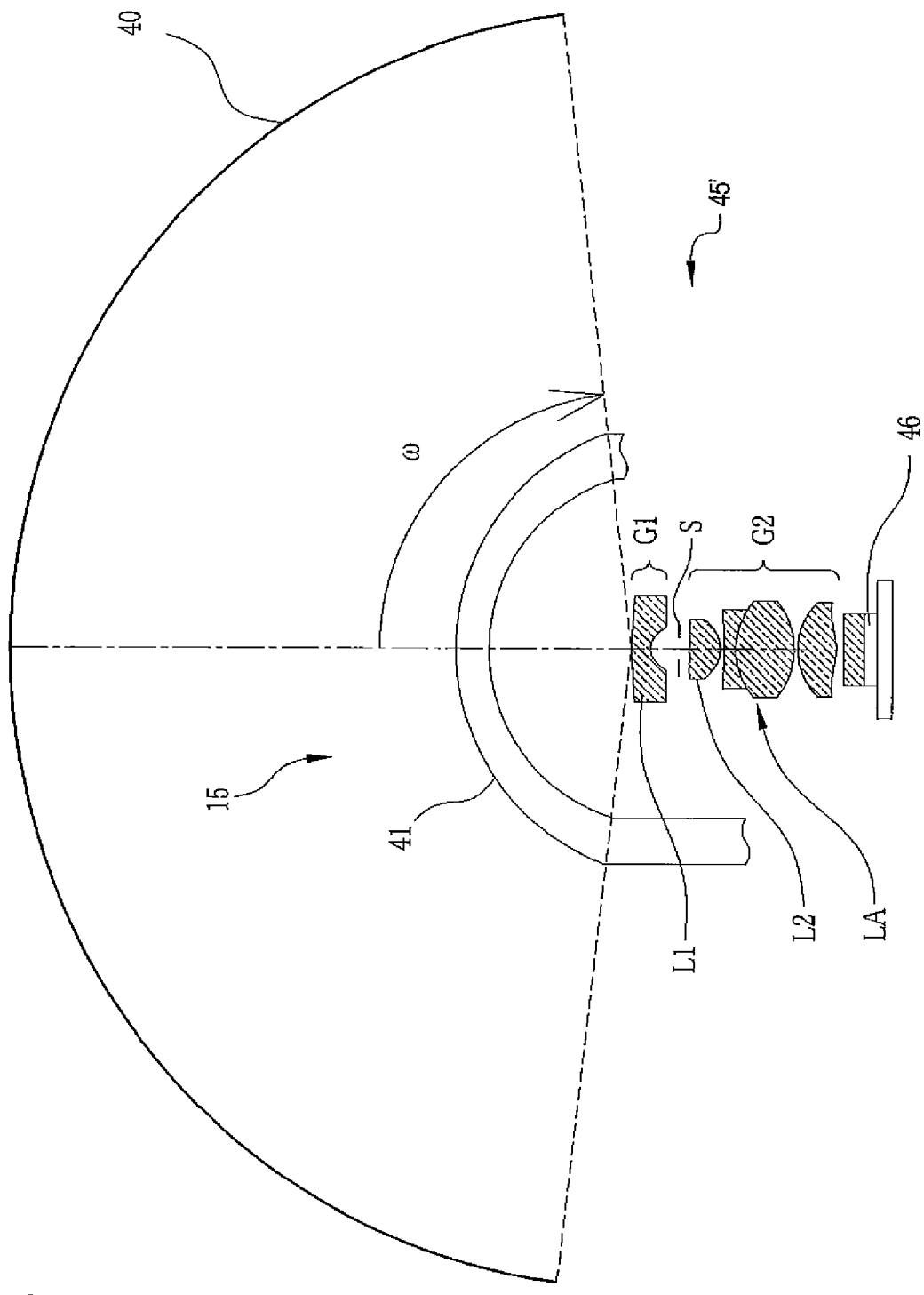
FIG. 4 is an explanatory view showing the imaging area of the capsule endoscope.

FIGS. 3 and 4 are explanatory views showing an imaging area of the capsule endoscope. In FIGS. 3 and 4, the configuration of the imaging lens systems 45 and 45' are different from each other.

As shown in FIGS. 3 and 4, the imaging lens systems 45 and 45' are configured so that an image is formed, in accordance with light from a spherical object 40, on the imaging surface of the imaging device 46 which is a plane surface. That is, the imaging lens systems 45 and 45' are configured so that when an image of a spherical object is taken, the image in the entire area from the center of the object to the periphery is formed in the substantially same plane. The imaging lens systems 45 and 45' are wide-angle such that the angle of the imaging area from the optical axis Z1, that is, the half angle of view ω is approximately 85 degrees at the maximum and that the entire angle of view 2ω is approximately 170 degrees at the maximum. The imaging lens systems 45 and 45' form images, in accordance with light from substantially the entire area of the front cover 41 formed in a spherical shape, on the imaging device 46.

It is not easy to control the posture of the capsule endoscope 15 when the capsule endoscope 15 is in the body of the patient 22. Therefore, it is desirable to provide an imaging lens system that is as wide-angle as possible so that images of lesions are surely taken. Thus, it is desirable that the imaging lens systems 45 and 45' be configured so that the following conditional expression is satisfied:

$$2\omega_{MAX} > 135 \text{ degrees}$$

where $\omega_{MAX}$ denotes the maximum half angle of view. When $2\omega_{MAX}$ is lower than 135 degrees, since it is not easy to control the posture of the capsule endoscope 15 in the body of the patient 22, the imaging lens system is unsuitable for an imaging lens system for the capsule endoscope, and there is a possibility that images of some parts might not be taken.

The imaging lens system 45 shown in FIG. 3 includes a first lens group G1 having a negative refractive power, an aperture diaphragm S, and a second lens group G2 having a positive refractive power. These are arranged in order of the first lens group G1, the aperture diaphragm S, and the second lens group G2 from the object side. In the imaging lens system 45, the total number of lenses included in the first lens group G1 and the second lens group G2 is four. The first lens group G1 includes one or two lenses, and the overall refractive power thereof is negative. The first lens group G1 is disposed on the most front side (most object side) of the imaging lens system 45. The second lens group G2 includes two or three lenses, and the overall refractive power thereof is positive. The second lens group G2 is disposed in rear (image side) of the first lens group G1 with the aperture diaphragm S being disposed therebetween.

The first lens L1 disposed on the most object side in the imaging lens system 45 is one of the lenses included in the first lens group G1. The first lens L1 has a meniscus shape and has a convex surface directed toward the object side. The curvatures of the surfaces of the first lens L1 are set so that the curvature of the image side surface is larger than that of the object side surface. The second lens L2, which is the second lens counted from the object side, is included in the first lens group G1 or the second lens group G2. The second lens L2 has a meniscus shape and has a convex surface directed toward the image side. The curvatures of the surfaces of the second lens L2 are set so that the curvature of the image side surface is larger than that of the object side surface.

The imaging lens system 45' shown in FIG. 4 includes a first lens group G1 having a negative refractive power, an aperture diaphragm S, and a second lens group 62 having a positive refractive power. These are arranged in order of the first lens group G1, the aperture diaphragm S, and the second lens group G2 from the object side. In the imaging lens system 45', the total number of lenses included in the first lens group G1 and the second lens group G2 is five. The first lens group G1 includes one or two lenses, and the overall refractive power thereof is negative. The first lens group G1 is disposed on the most front side (most object side) of the imaging lens system 45'. The second lens group G2 includes two to four lenses, and the overall refractive power thereof is positive. The second lens group G2 is disposed in rear (image side) of the first lens group G1 with the aperture diaphragm S being disposed therebetween.

The first lens L1 disposed on the most object side in the imaging lens system 45' is one of the lenses included in the first lens group G1. The first lens L1 has a meniscus shape and a convex surface directed toward the object side. The curvatures of the surfaces of the first lens L1 are set so that the curvature of the image side surface is larger than that of the object side surface. The second lens L2, which is the second lens counted from the object side, is included in the first lens group 61 or the second lens group 62. The second lens L2 has a meniscus shape and has a convex surface directed toward the image side. The curvatures of the surfaces of the second lens L2 are set so that the curvature of the image side surface is larger than that of the object side surface.

The second lens group G2 also includes an achromatic lens LA formed by cementing two lenses. The achromatic lens LA is formed by cementing lenses made of materials having different refractive indices such as crown glass and flint glass. The achromatic lens LA reduces chromatic aberration of the imaging lens system 45'.

Further, the imaging lens systems 45 and 45' are configured so that the following conditional expression (1) is satisfied with respect to an arbitrary half angle of view ω:

$$0.7 < \frac{Y(\omega + \Delta\omega) - Y(\omega)}{Y(\Delta\omega)} \tag{1}$$

where Y(ω) denotes an image height at a point of an angle of view ω,

Δω denotes the amount of minute change of the angle of view from the point of the angle of view ω.

The conditional expression (1) defines the degree of distortion caused by the imaging lens systems 45 and 45', which form an image of a spherical object in a plane. If $$\frac{Y(\omega + \Delta\omega) - Y(\omega)}{Y(\Delta\omega)}$$

falls below the lower limit, distortion becomes too large. Therefore, the image height becomes too small in the peripheral part of the taken image. Consequently, there is a possibility that a lesion in that part might be overlooked at the time of diagnosis.

Figure 5:
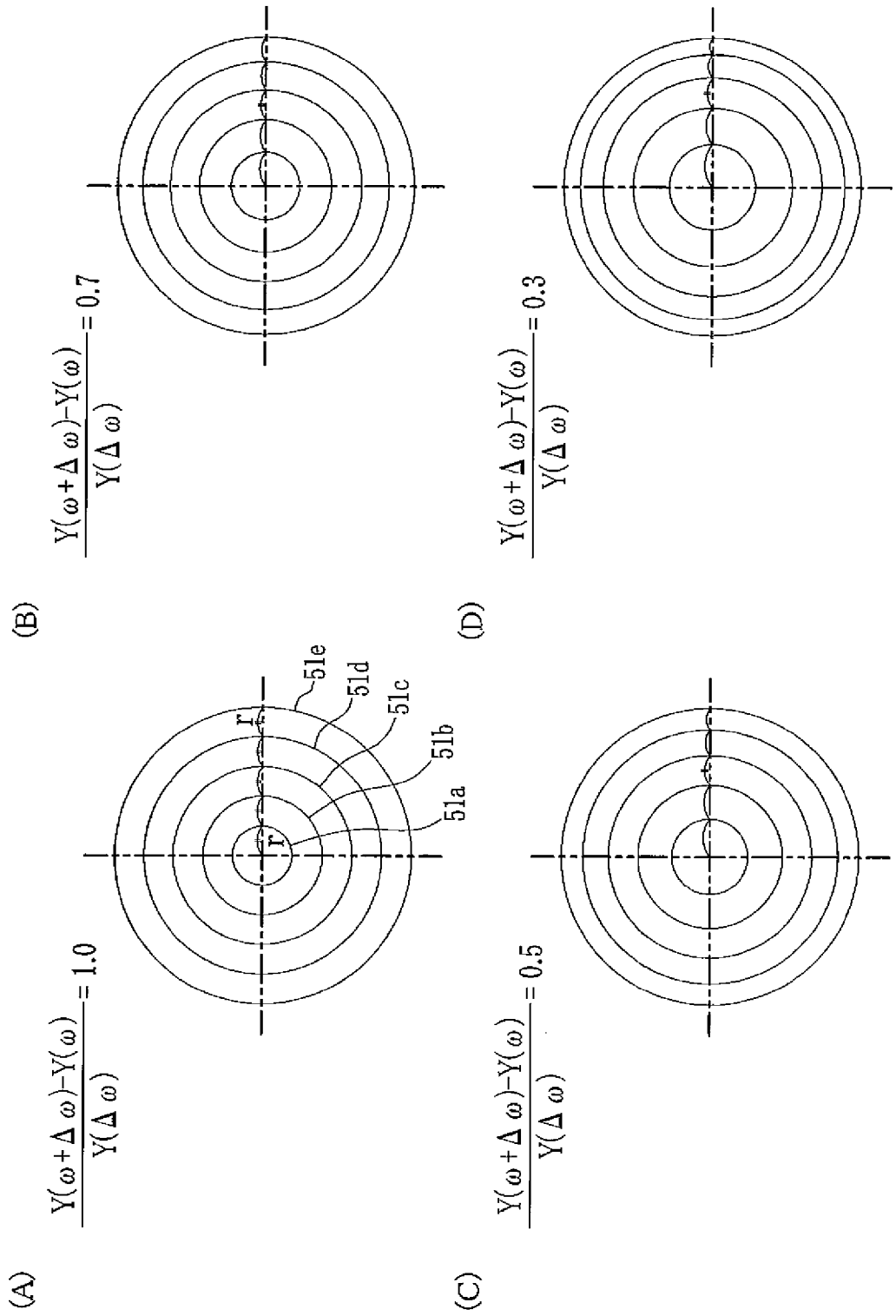
FIG. 5 is an explanatory view showing an example of distortion which is caused when an image of a spherical object is formed in a plane.

When an image of a spherical object having uniformly spaced annular patterns is taken by using the imaging lens systems 45 or 45', as shown in FIG. 5(A), in the case of $$\frac{Y(\omega + \Delta\omega) - Y(\omega)}{Y(\Delta\omega)} = 1.0,$$

uniformly spaced concentric patterns 51a to 51e are formed in the image. At this time, when the radius of the smallest circular pattern 51a is r, the radii of the circular patterns 51b to 51e are 2r, 3r, 4r, and 5r, respectively, and the distances between the adjacent circular patterns are r. That is, in the case of $$\frac{Y(\omega + \Delta\omega) - Y(\omega)}{Y(\Delta\omega)} = 1.0,$$

no distortion is caused, and an image of a lesion in the peripheral part of the taken image is the same in size and shape as an image when the lesion is taken from its front side.

On the other hand, as shown in FIG. 5(B), in the case of $$\frac{Y(\omega + \Delta\omega) - Y(\omega)}{Y(\Delta\omega)} = 0.7,$$

since the imaging angle of view is fixed, the circular pattern 51e having the largest radius is imaged to have the same size and the same shape as that when there is no distortion. However, the circular patterns 51a to 51d having smaller radii than the circular pattern 51e are all images to have larger sizes than images when there is no distortion. At this time, the radius of the circular pattern 51a having the smallest radius is larger than r, and the distance between the circular pattern 51a and the circular pattern 51b is larger than r. Also, the distance between the circular pattern 51b and the circular pattern 51c is equal to r. On the other hand, the distance between the circular pattern 51c and the circular pattern 51d is smaller than r, and the distance between the circular pattern 51d and the circular pattern 51e is smaller than that between the circular pattern 51c and the circular pattern 51d.

However, in the case of a distortion of $$\frac{Y(\omega + \Delta\omega) - Y(\omega)}{Y(\Delta\omega)} = \text{about } 0.7,$$

even when a lesion is shown in the peripheral part of the image, the image of the lesion is not reduced or distorted to the extent that the lesion is overlooked.

As shown in FIG. 5(C), in the case of $$\frac{Y(\omega + \Delta\omega) - Y(\omega)}{Y(\Delta\omega)} = 0.5,$$

the reduction of the distances between the circular patterns in the peripheral part of the image is more conspicuous. Therefore, there is a possibility that a lesion might be overlooked when the lesion is shown in the peripheral part of the image.

Further, as shown in FIG. 5(D), in the case of $$\frac{Y(\omega + \Delta\omega) - Y(\omega)}{Y(\Delta\omega)} = 0.3,$$

the reduction of the distances between the circular patterns in the peripheral part of the image is extremely conspicuous, so that there is a possibility that even a comparatively large lesion that should be easily found when observed from its front side is extremely reduced and distorted, and might be overlooked when the lesion is shown in the peripheral part of the image.

As described above, the influence of distortion in the peripheral part of an image becomes more conspicuous as the value of $$\frac{Y(\omega + \Delta\omega) - Y(\omega)}{Y(\Delta\omega)}$$

is smaller as compared with 1.0. Therefore, it is preferable that the imaging lens systems 45 and 45' forming an image of a spherical object in a plane satisfy the conditional expression (1). That is, it is preferable that the value of $$\frac{Y(\omega + \Delta\omega) - Y(\omega)}{Y(\Delta\omega)}$$

be larger than 0.7 with respect to a given half angle of view ω. It is more preferable that the value of $$\frac{Y(\omega + \Delta\omega) - Y(\omega)}{Y(\Delta\omega)}$$

be larger than 0.7 and smaller than 1.3, and it is further preferable that the value be larger than 0.8 and smaller than 1.2 with respect to a given half angle of view ω. Moreover, it is particularly preferable e that the absolute value of $$\frac{Y(\omega + \Delta\omega) - Y(\omega)}{Y(\Delta\omega)}$$

be as close to 1.0 as possible with respect to a given half angle of view ω.

Specific examples of the imaging lens system 45 including for lenses and satisfying the conditional expression (1) will be described as Examples 1 and 2, and a specific example of the imaging lens system 45' including five lenses and satisfying the conditional expression (1) will be described as Example 3.

EXAMPLE 1

Figure 6:
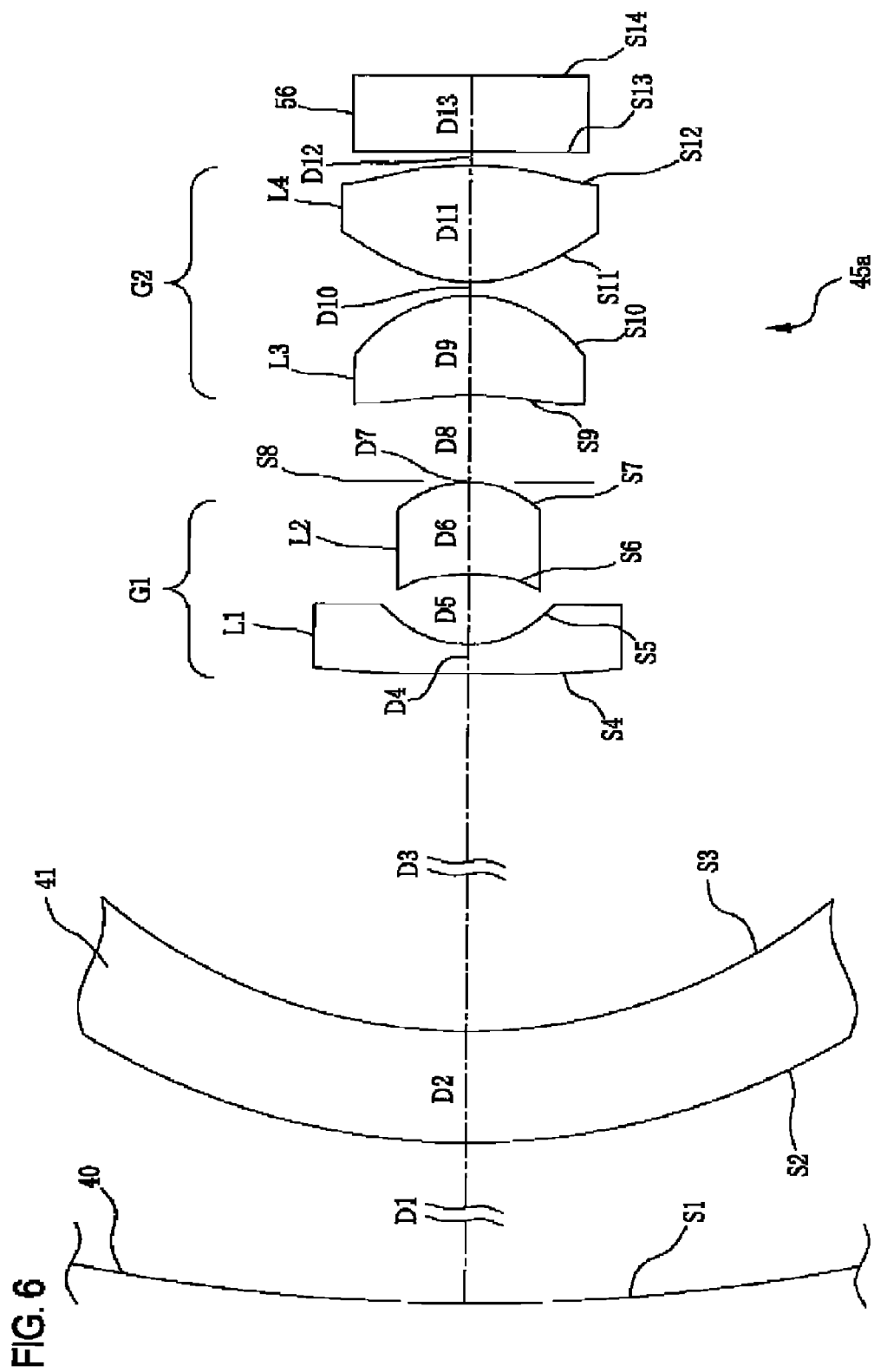
FIG. 6 is a section view showing the configuration of an imaging lens system of Example 1.

As shown in FIG. 6, an imaging lens system 45a includes, in order from the object side, a first lens L1 having a meniscus shape and having a convex surface directed to the object side, a second lens L2 having a meniscus shape and having a convex surface directed to the image side (imaging device side), an aperture diaphragm, a third lens L3 having a meniscus shape and a convex surface directed toward the image side, and a fourth lens L4 having a biconvex shape. A first lens group G1 of the imaging lens system 45a includes the first lens L1 and the second lens L2, which are disposed on the object side of the aperture diaphragm. The overall refractive power of the first lens group G1 is negative. A second lens group G2 of the imaging lens system 45a includes the third lens L3 and the fourth lens L4, which are disposed on the image side of the aperture diaphragm. The overall refractive power of the second lens group G2 is positive. The surface shapes and arrangement of these lenses L1 to L4 are set in consideration of the front cover 41 and a cover glass 56 of the imaging device 46.

Also, the surface of the spherical object is designated by S1, the object side surface of the front cover 41 is designated by S2, the image side surface of the front cover 41 is designated by S3, the object side surface of the first lens L1 is designated by S4, the image side surface of the first lens L1 is designated by S5, the object side surface of the second lens L2 is designated by S6, the image side surface of the second lens L2 is designated by S7, the aperture diaphragm is designated by S8, the object side surface of the third lens L3 is designated by S9, the image side surface of the third lens L3 is designated by S10, the object side surface of the fourth lens L4 is designated by S11, the image side surface of the fourth lens L4 is designated by S12, the object side surface of the cover glass 56 is designated by S13, and the image side surface of the cover glass 56 is designated by S14. These surfaces are each designated by the surface Si (surface number i=1 to 14). The imaging surface of the imaging device 46 coincides with the surface S14. The distance on the optical axis Z1 (on-axis surface separation) between the surface Si and the adjacent surface Si+1 on the image side is represented by Di (i=1 to 13).

As lens data of the imaging lens system 45a, the radii of curvature Ri of the surfaces Si, the on-axis surface separations Di, and the refractive indices Nd and the Abbe numbers vd of the front cover 41, the lenses L1 to L4, and the cover glass 56 at the d-line (wavelength 587.6 nm) are shown in Table 1. The F-number, the focal length f, and the angle of view 2ω (degrees) of the imaging lens system 45a are also shown in a lower part of Table 1. This lens data (Table 1) is lens data when normalization is performed so that the value of the focal length f becomes 1.0. The surfaces Si, which are aspheric, are marked with *.

The specific configurations of the aspheric surfaces Si are expressed by the following expression (2) using the curvature c (the reciprocal of the paraxial radius of curvature R), the conic constant K, the distance $\rho(\rho^2=x^2+y^2)$ from the optical axis, and the i-th aspheric coefficient Ai. For the aspheric surfaces Si, the conic constant K and the respective aspheric coefficients Ai are shown in Table 2. The expression, which defines the configurations of the aspheric surfaces, is the same in the second and third examples described later.

TABLE 1

| | Surface number i | Ri | Di | $N_d$ | $v_d$ |
|---|---|---|---|---|---|
| (object) | 1 | 28.2332 | 19.4022 | | |
| | 2 | 10.1884 | 1.4572 | 1.57500 | 32.2 |
| | 3 | 7.8196 | 6.2476 | | |
| | 4* | −117.6982 | 0.3795 | 1.53039 | 55.2 |
| | 5* | 1.5604 | 0.9144 | | |
| | 6* | −3.3005 | 1.1967 | 1.53039 | 55.2 |
| | 7* | −1.3610 | 0.0054 | | |
| (AD) | 8 | ∞ | 1.1230 | | |
| | 9* | −4.3483 | 1.2890 | 1.53039 | 55.2 |
| | 10* | −1.8179 | 0.1822 | | |
| | 11* | 1.8940 | 1.5094 | 1.53039 | 55.2 |
| | 12* | −4.3858 | 0.1761 | | |
| (cover glass) | 13 | ∞ | 0.9927 | 1.55920 | 53.9 |
| | 14 | ∞ | 0.0000 | | |
| (imaging surface) | | ∞ | | | |

(AD: Aperture Diaphragm)
F Number 1.4
Focal length f 1.0
Angle of view 2ω (degree) 168.0

$$z = \frac{c\rho^2}{1+\sqrt{1-(K+1)c^2\rho^2}} + \sum_i A_i \rho^i \quad (\rho^2 = x^2 + y^2) \tag{2}$$

TABLE 2

| Surface number i | K | $A_3$ | $A_4$ | $A_5$ | $A_6$ |
|---|---|---|---|---|---|
| 4 | −1.0000 | 6.4662E−03 | −1.0823E−03 | 1.2994E−03 | 1.277E−03 |
| 5 | −1.0000 | 4.3222E−02 | 1.2853E−02 | 5.3203E−03 | −5.3685E−03 |
| 6 | −1.0000 | −5.0859E−03 | −3.4693E−02 | −1.3680E−02 | −3.1221E−02 |
| 7 | −1.0000 | 5.8988E−03 | −1.7335E−02 | 1.1859E−02 | −1.8205E−02 |
| 9 | −1.0000 | 2.1280E−02 | 4.9107E−03 | 2.8814E−02 | −1.7732E−02 |
| 10 | −1.0000 | −2.3316E−02 | 2.6397E−03 | 2.5619E−03 | 4.5554E−04 |
| 11 | −1.0000 | −2.7029E−02 | 5.8249E−03 | 2.6211E−04 | −3.8849E−03 |
| 12 | −1.0000 | 1.2528E−02 | −4.9044E−03 | 2.6159E−03 | −5.5300E−04 |

| Surface number i | $A_7$ | $A_8$ | $A_9$ | $A_{10}$ | $A_{11}$ |
|---|---|---|---|---|---|
| 4 | −8.3443E−04 | −2.3103E−04 | 1.5397E−04 | 1.5083E−06 | 1.3272E−08 |
| 5 | −3.5806E−03 | 2.6181E−03 | 7.1885E−06 | 2.8852E−07 | 5.6322E−09 |
| 6 | −4.7545E−03 | −3.3105E−03 | −6.5527E−06 | −4.0152E−08 | 5.7187E−09 |
| 7 | 4.2313E−03 | −2.8733E−04 | 1.9037E−06 | 1.0417E−07 | 5.7187E−09 |
| 9 | 1.3438E−05 | −1.4280E−03 | 3.4946E−04 | 4.5382E−07 | 5.7187E−09 |
| 10 | −3.3893E−04 | −8.8711E−04 | −5.6674E−04 | 1.5669E−07 | 5.7187E−09 |
| 11 | 1.9742E−03 | 7.5091E−05 | −6.1615E−04 | 7.6879E−05 | 3.0862E−07 |
| 12 | −7.6048E−04 | 7.9145E−05 | 4.1644E−04 | 1.1190E−04 | 4.3744E−08 |

TABLE 2-continued

| Surface number i | $A_{12}$ | $A_{13}$ | $A_{14}$ | $A_{15}$ | $A_{16}$ |
|---|---|---|---|---|---|
| 4 | 3.5637E−10 | 1.9565E−11 | 9.4627E−13 | 5.1950E−14 | 2.8521E−15 |
| 5 | 3.1396E−10 | 1.7236E−11 | 9.4627E−13 | 5.1950E−14 | 2.8521E−15 |
| 6 | 3.1396E−10 | 1.7236E−11 | 9.4627E−13 | 5.1950E−14 | 2.8521E−15 |
| 7 | 3.1396E−10 | 1.7236E−11 | 9.4627E−13 | 5.1950E−14 | 2.8521E−15 |
| 9 | 3.1396E−10 | 1.7236E−11 | 9.4627E−13 | 5.1950E−14 | 2.8521E−15 |
| 10 | 3.1396E−10 | 1.7236E−11 | 9.4627E−13 | 5.1950E−14 | 2.8521E−15 |
| 11 | 3.1680E−10 | 1.7236E−11 | 9.4627E−13 | 5.1950E−14 | 2.8521E−15 |
| 12 | 3.1388E−10 | 1.7236E−11 | 9.4627E−13 | 5.1950E−14 | 2.8521E−15 |

| Surface number i | $A_{17}$ | $A_{18}$ | $A_{19}$ | $A_{20}$ |
|---|---|---|---|---|
| 4 | 1.5658E−16 | 8.5961E−18 | 4.7193E−19 | 2.5909E−20 |
| 5 | 1.5658E−16 | 8.5961E−18 | 4.7193E−19 | 2.5909E−20 |
| 6 | 1.5658E−16 | 8.5961E−18 | 4.7193E−19 | 2.5909E−20 |
| 7 | 1.5658E−16 | 8.5961E−18 | 4.7193E−19 | 2.5909E−20 |
| 9 | 1.5658E−16 | 8.5961E−18 | 4.7195E−19 | 2.5909E−20 |
| 10 | 1.5658E−16 | 8.5961E−18 | 4.7193E−19 | 2.5909E−20 |
| 11 | 1.5658E−16 | 8.5961E−18 | 4.7193E−19 | 2.5909E−20 |
| 12 | 1.5658E−16 | 8.5961E−18 | 4.7193E−19 | 2.5909E−20 |

Figure 7:
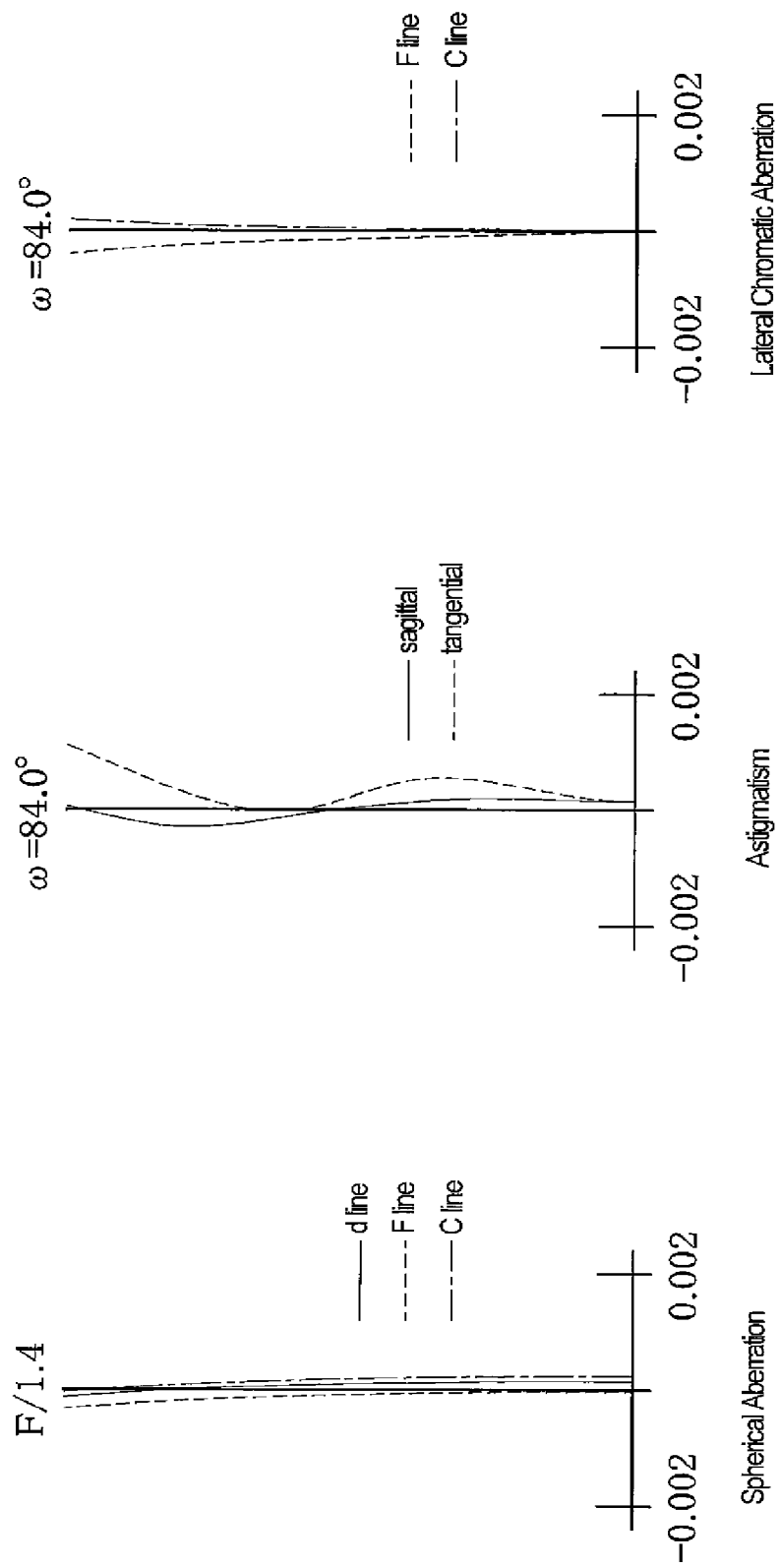
FIG. 7 shows graphic representations of aberrations of the imaging lens system of Example 1.

Further, the spherical aberrations, the astigmatisms, and the lateral chromatic aberrations of the imaging lens system 45a are shown in FIG. 7. These aberration diagraphs show aberrations when the front cover 41 and the cover glass 56 shown in Table 1 are provided. The spherical aberration at the d-line (wavelength 587.6 nm) is represented by the solid line, the spherical aberration at the F-line (wavelength 486.13 nm) is represented by the broken line, and the spherical aberration at the C-line (wavelength 656.27 nm) is represented by the alternate long and short dash line. The astigmatism in the sagittal direction is represented by the solid line, and the astigmatism in the tangential direction is represented by the broken line. The lateral chromatic aberration at the F-line is represented by the broken line, and the lateral chromatic aberration at the C-line is represented by the alternate long and short dash line. The way of representation of these aberrations is similar in the Examples 2 and 3 described later.

Figure 8:
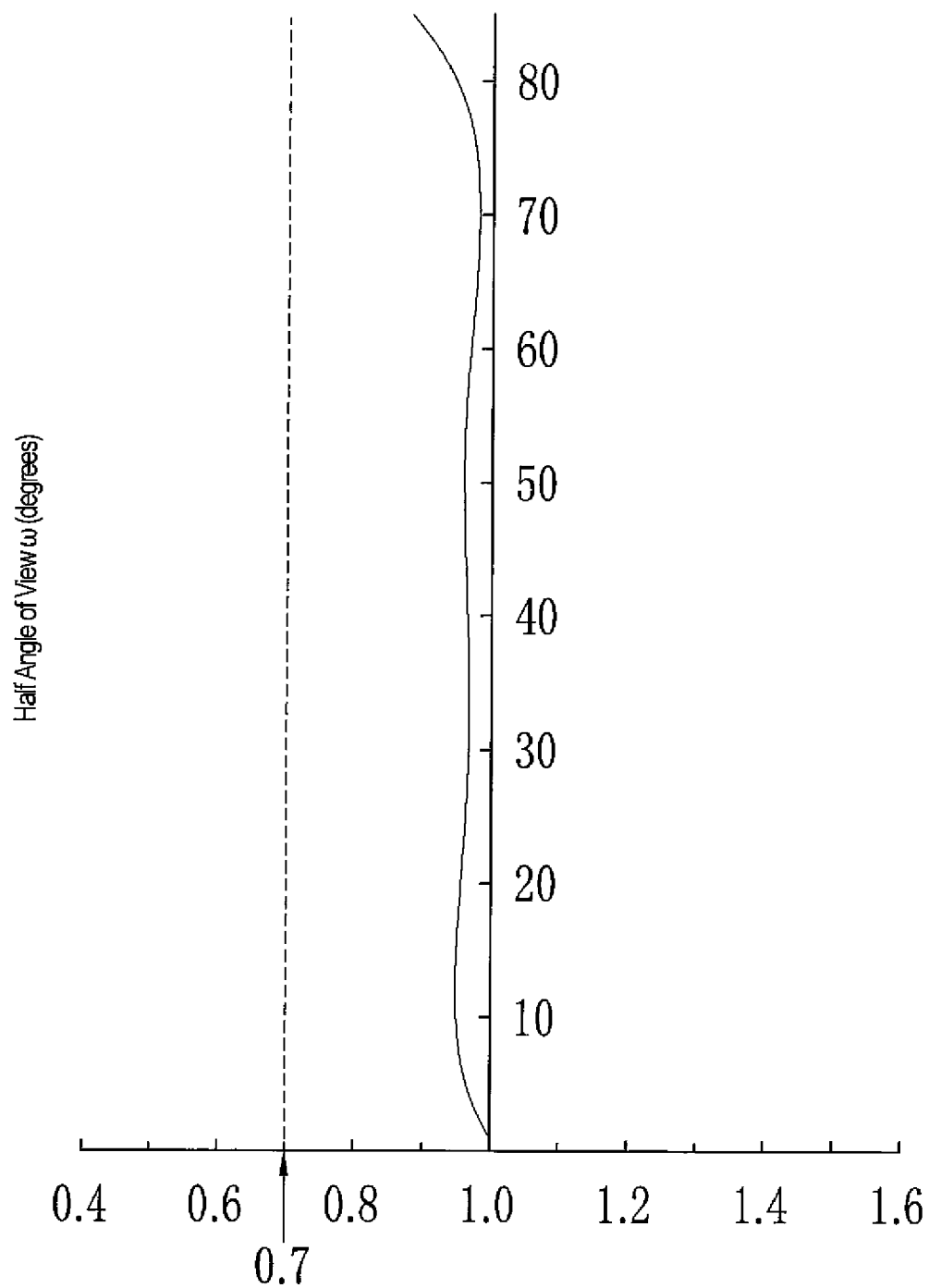
FIG. 8 is a graph showing distortion of the imaging lens system of Example 1.

As shown in FIG. 8, the imaging lens system 45a satisfies the conditional expression (1) with respect to a given angle of view ω, and the value of $$\frac{Y(\omega + \Delta\omega) - Y(\omega)}{Y(\Delta\omega)}$$

is larger than 0.7 and close to 1.0 in the entire range of the half angle of view ω of 0 to 84.0 degrees. Therefore, in the images of spherical objects taken by the imaging lens system 45a, the image reduction and distortion are small even in the peripheral part. That is, although the imaging lens system 45a is a wide-angle lens whose maximum angle of view $2\omega_{MAX}$ is as large as 168.0 degrees, in the images taken by this lens system, distortion that leads to lesion overlooking is not caused in the entire area including the peripheral part.

As described above, since the imaging lens system 45a includes four lenses, in particular, since the imaging lens system 45a has a two-group, four-lens configuration as mentioned above, distortion is excellently corrected in the entire range of the angle of view $2\omega_{MAX}$ without increase in the size of the capsule endoscope. Therefore, by mounting the imaging lens system 45a, a capsule endoscope can be obtained that is wide-angle and has its distortion improved even in the peripheral part of an image while maintaining an easy-to-swallow size.

EXAMPLE 2

Figure 9:
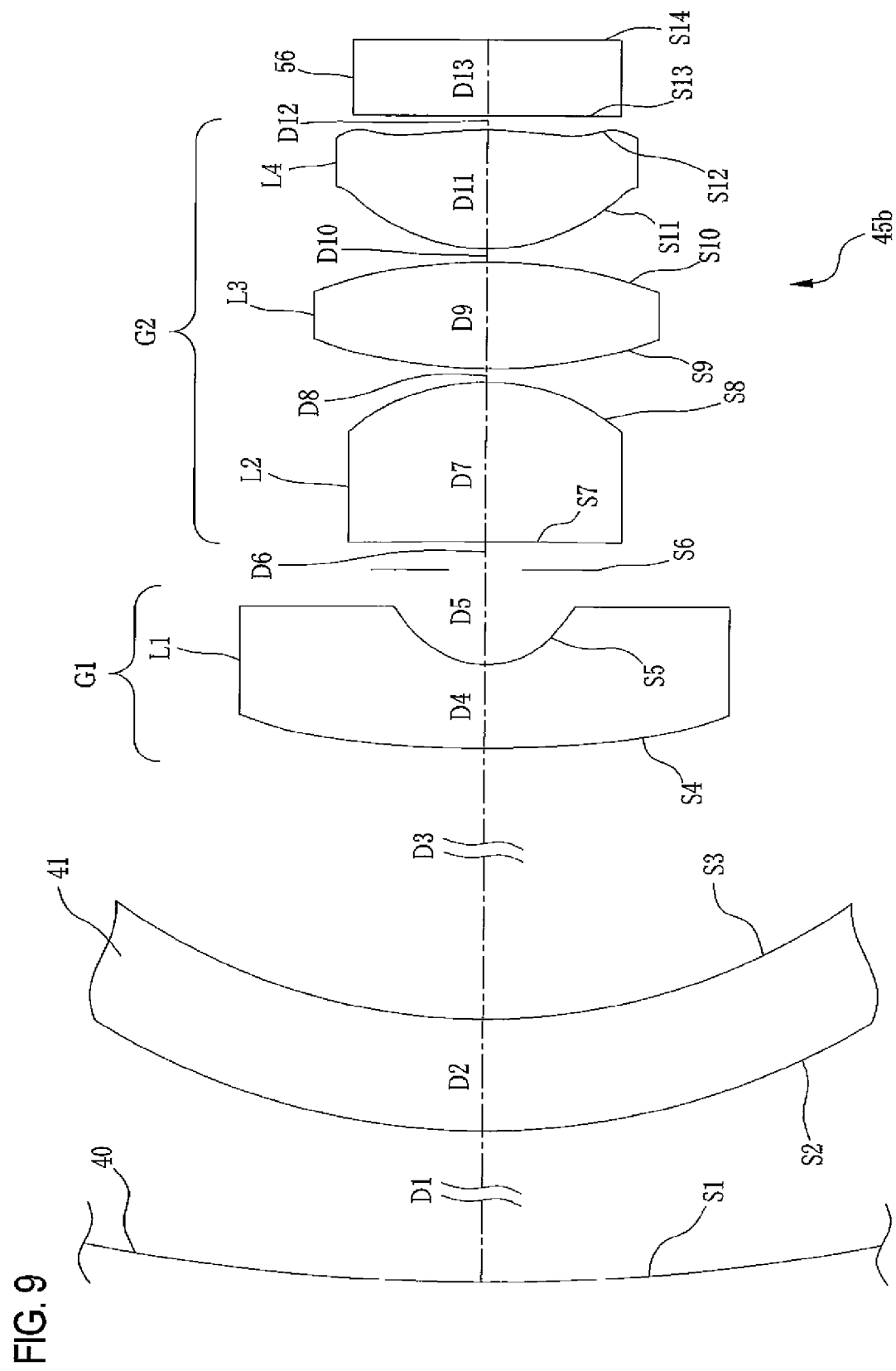
FIG. 9 is a section view showing the configuration of an imaging lens system of Example 2.

As shown in FIG. 9, a imaging lens system 45b includes, in order from the object side, a first lens L1 having a meniscus shape and having a convex surface directed toward the object side; an aperture diaphragm, a second lens L2 having a convex surface directed toward the image side, a third lens L3 having a biconvex shape, and a fourth lens L4 having a biconvex shape. A first lens group G1 of the imaging lens system 45b includes the first lens L1 deposed on the object side of the aperture diaphragm. The refractive power of the first lens group G1 is negative. A second lens group G2 of the imaging lens system 45b includes the second lens L2, the third lens L3, and the fourth lens L4, which are disposed on the image side of the aperture diaphragm. The overall refractive power of the second lens group G2 is positive. The surface shapes and arrangement of these lenses L1 to L4 are set in consideration of the front cover 41 and the cover glass 56 of the imaging device 46.

The surface of the spherical object is designated by S1, the object side surface of the front cover 41 is designated by S2, the image side surface of the front cover 41 is designated by S3, the object side surface of the first lens L1 is designated by S4, the image side surface of the first lens L1 is designated by S5, the aperture diaphragm is designated by S6, the object side surface of the second lens L2 is designated by S7, the image side surface of the second lens L2 is designated by S8, the object side surface of the third lens L3 is designated by S9, the image side surface of the third lens L3 is designated by S10, the object side surface of the fourth lens L4 is designated by S11, the image side surface of the fourth lens L4 is designated by S12, the object side surface of the cover glass 56 is designated by S13, and the image side surface of the cover glass 56 is designated by S14. These surfaces are each designated by the surface Si (surface number i=1 to 14). The imaging surface of the imaging device 46 coincides with the surface S14. The distance on the optical axis Z1 (on-axis surface separation) between the surface Si and the adjacent surface Si+1 on the image side is represented by Di (i=1 to 13).

As lens data of the imaging lens system 45b, the radii of curvature Ri of the surfaces Si, the on-axis surface separations Di, and the refractive indices Nd and the Abbe numbers vd of the front cover 41, the lenses L1 to L4, and the cover glass 56 at the d-line (wavelength 587.6 nm) are shown in Table 3. The F number, the focal length f, and the angle of view 2ω (degrees) of the imaging lens system 45b are also shown in a lower part of Table 3. This lens data (Table 3) of the imaging lens system 45b is lens data when normalization is performed so that the value of the focal length f becomes 1.0. The surfaces Si that are aspheric are marked with *.

The specific configurations of the aspheric surfaces are expressed by the same expression (2) as in Example 1. For the aspheric surfaces Si, the conic constant K and the respective aspheric coefficients Ai are shown in Table 4.

Figure 10:
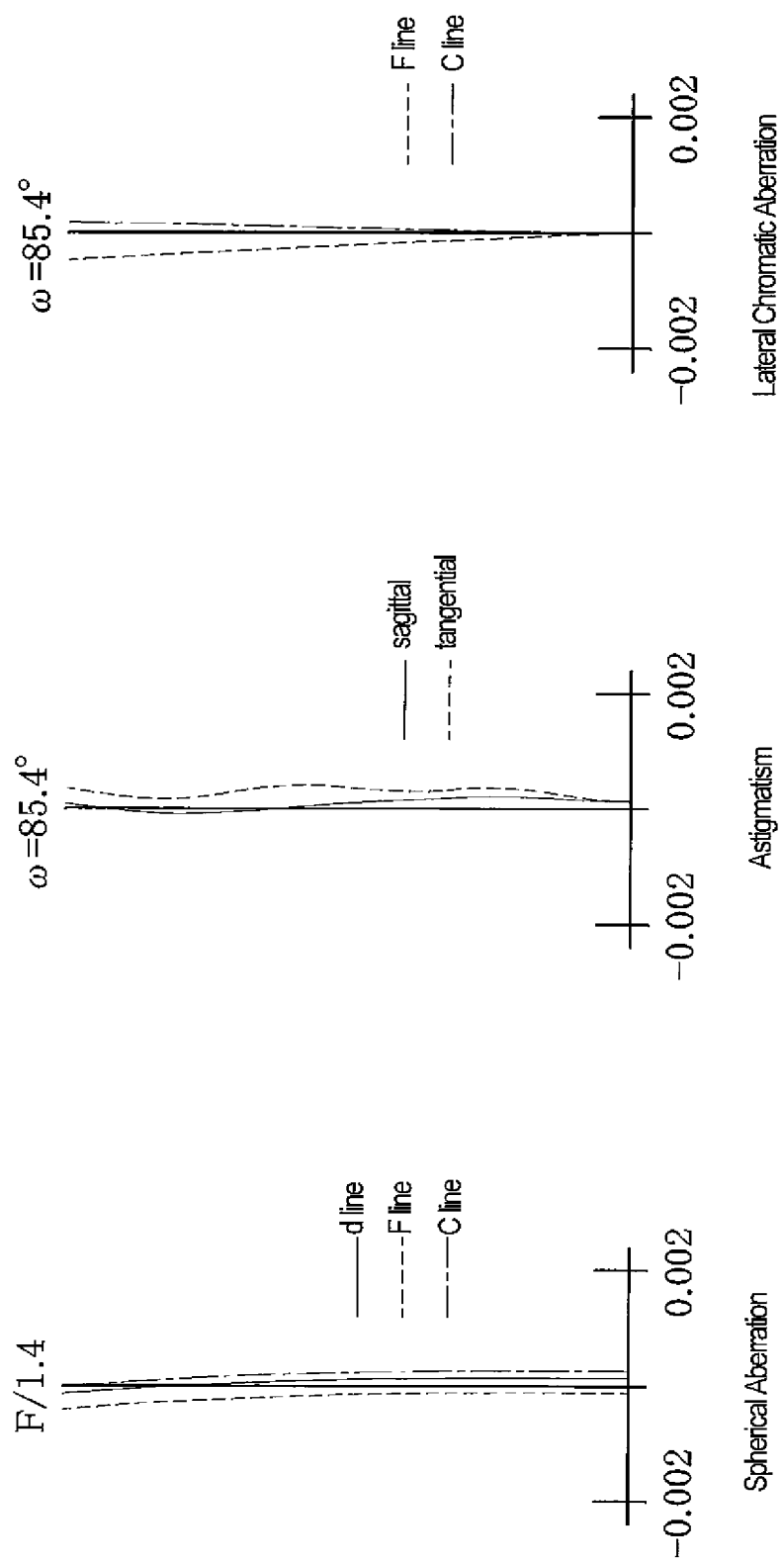
FIG. 10 shows graphic representations of aberrations of the imaging lens system of Example 2.

Further, the spherical aberrations, the astigmatisms, and the lateral chromatic aberrations of the imaging lens system 45b are shown in FIG. 10. These aberration diagraphs show aberrations when the front cover 41 and the cover glass 56 shown in Table 3 are provided. The way of representation of these aberrations is similar to that of Example 1.

Figure 11:
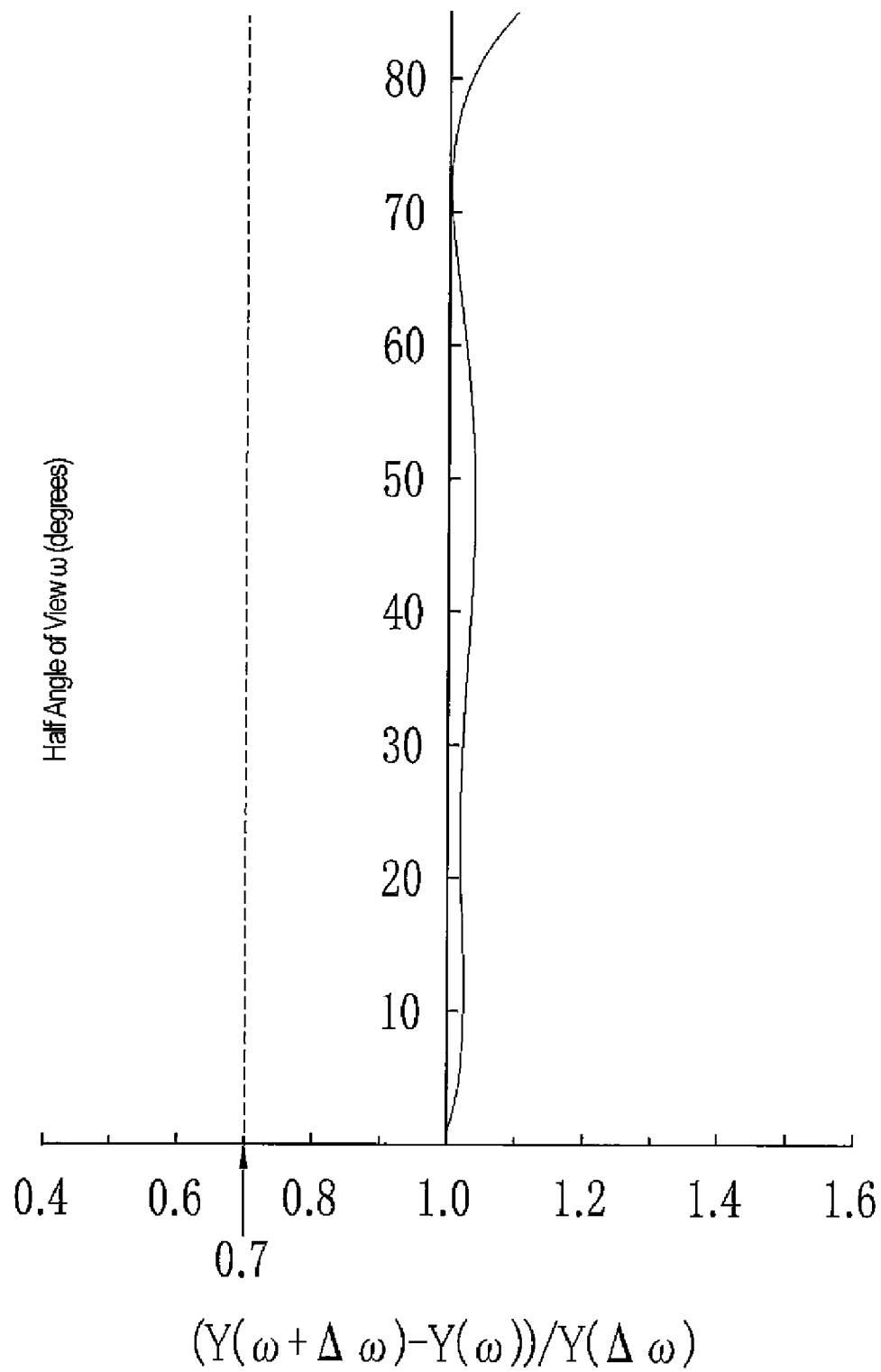
FIG. 11 is a graph showing distortion of the imaging lens system of Example 2.

As shown in FIG. 11, the imaging lens system 45b satisfies the conditional expression (1) with respect to a given angle of view ω, and the value of $$\frac{Y(\omega + \Delta\omega) - Y(\omega)}{Y(\Delta\omega)}$$

is larger than 0.7 and close to 1.0 in the entire range of the half angle of view ω of from 0 degree to 84.0 degrees. Therefore, in images of spherical objects taken by the imaging lens system 45b, the image reduction and distortion are small even in the peripheral part. That is, although the imaging lens system 45b is a wide-angle lens whose maximum angle of view $2\omega_{MAX}$ is as large as 170.0 degrees, in images taken by this imaging lens system, a distortion that leads to lesion overlooking is not caused in the entire area including the peripheral part.

As described above, since the imaging lens system 45b includes four lenses, in particular, since the imaging lens system 45b has a two-group, four-lens configuration as mentioned above, distortion is excellently corrected in the entire range of the angle of view $2\omega_{MAX}$ without increase in the size of the capsule endoscope. Therefore, by mounting the imaging lens system 45b, a capsule endoscope is obtained that is wide-angle and has its distortion improved even in the peripheral part of the image while maintaining an easy-to-swallow size.

TABLE 3

| Surface number i | | Ri | Di | $N_d$ | $v_d$ |
|---|---|---|---|---|---|
| (object) | 1 | 29.0057 | 16.9570 | | |
| | 2 | 10.2579 | 1.4971 | 1.57500 | 32.2 |
| | 3 | 8.7517 | 5.8627 | | |
| | 4* | 21.0846 | 1.1291 | 1.53039 | 55.2 |
| | 5* | 1.2635 | 1.2642 | | |
| (AD) | 6 | ∞ | 0.3829 | | |
| | 7 | −21.3026 | 2.1301 | 1.80400 | 46.6 |
| | 8 | −3.0244 | 0.1873 | | |
| | 9 | 7.5453 | 1.4255 | 1.80400 | 46.6 |
| | 10 | −7.1995 | 0.1865 | | |
| | 11* | 2.6921 | 1.5813 | 1.53039 | 55.2 |
| | 12* | −4.0858 | 0.1871 | | |
| (cover glass) | 13 | ∞ | 1.0199 | 1.55920 | 53.9 |
| | 14 | ∞ | 0.0000 | | |
| (imaging surface) | | ∞ | | | |

(AD: Aperture Diaphragm)
F Number  1.4
Focal length f  1.0
Angle of view 2ω (degree)  170.8

TABLE 4

| Surface number i | K | $A_3$ | $A_4$ | $A_5$ | $A_6$ |
|---|---|---|---|---|---|
| 4 | −1.0000 | 1.1806E−03 | 6.0847E−04 | 1.1648E−04 | 1.1526E−05 |
| 5 | −1.0000 | 3.0189E−02 | 2.9023E−02 | −1.1704E−03 | −1.1450E−04 |
| 11 | −1.0000 | 6.2958E−03 | −6.0490E−03 | 3.8647E−03 | 1.3835E−03 |
| 12 | −1.0000 | 4.0413E−02 | 1.1306E−02 | 2.8963E−03 | 1.6035E−03 |

| Surface number i | $A_7$ | $A_8$ | $A_9$ | $A_{10}$ | $A_{11}$ |
|---|---|---|---|---|---|
| 4 | −3.1849E−07 | −5.5674E−07 | −1.9003E−07 | −4.4059E−08 | −6.2540E−09 |
| 5 | 3.8652E−03 | 4.5996E−03 | 3.2054E−03 | 1.5331E−03 | 4.4516E−04 |
| 11 | 9.1107E−05 | −1.2677E−04 | −7.7351E−05 | −2.3361E−05 | −8.6265E−08 |
| 12 | 9.4610E−04 | 4.0676E−04 | 9.5714E−05 | −3.5343E−05 | −6.5696E−05 |

| Surface number i | $A_{12}$ | $A_{13}$ | $A_{14}$ | $A_{15}$ | $A_{16}$ |
|---|---|---|---|---|---|
| 4 | 3.8526E−10 | 6.0256E−10 | 1.8528E−10 | 1.0491E−11 | −3.7667E−12 |
| 5 | −5.1892E−05 | −2.0610E−04 | −2.1831E−04 | −1.9444E−04 | −3.3983E−05 |
| 11 | 5.3226E−06 | 4.3320E−06 | 2.3286E−06 | 8.4037E−07 | 3.8252E−08 |
| 12 | −5.5364E−05 | −3.5172E−05 | −1.7641E−05 | −5.8258E−06 | 8.5904E−07 |

| Surface number i | $A_{17}$ | $A_{18}$ | $A_{19}$ | $A_{20}$ |
|---|---|---|---|---|
| 4 | −6.3129E−13 | −1.3027E−13 | −2.5007E−15 | 3.8559E−15 |
| 5 | −2.3424E−07 | −1.2454E−07 | 0.0000E+00 | 3.9978E−20 |
| 11 | −2.8889E−07 | −3.6116E−07 | −1.7141E−08 | 0.0000E+00 |
| 12 | 3.9596E−06 | 1.5778E−07 | 0.0000E+00 | 0.0000E+00 |

EXAMPLE 3

Figure 12:
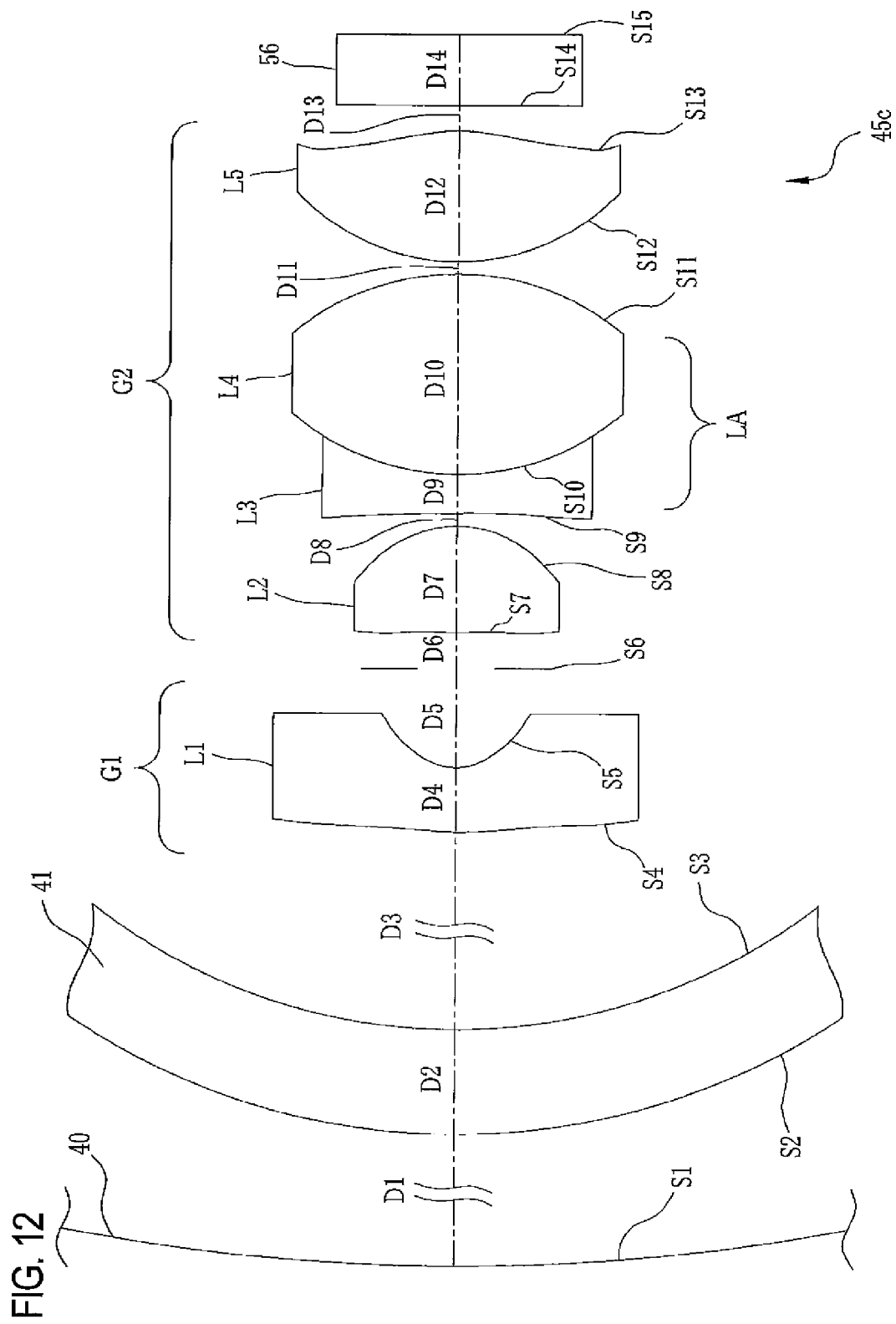
FIG. 12 is a section view showing the configuration of an imaging lens system of Example 3.

As shown in FIG. 12, a imaging lens system 45c includes, in order from the object side, a first lens L1 having a meniscus shape and having a convex surface directed toward the object side, an aperture diaphragm, a second lens L2 having a biconvex shape, a third lens L3 having a biconcave configuration, a fourth lens L4 having a biconvex shape, and a fifth lens L5 having a biconvex shape. A first lens group G1 of the imaging lens system 45c includes the first lens L1 deposed on the object side of the aperture diaphragm. The refractive power of the first lens group G1 is negative. A second lens group G2 of the imaging lens system 45c includes the second lens L2, the third lens L3, the fourth lens L4, and the fifth lens L5, which are disposed on the image side of the aperture diaphragm. The overall refractive power of the second lens group G2 is positive. Further, the opposed surfaces of the third lens L3 and the fourth lens L4 are cemented to form an achromatic lens LA. The surface shapes and arrangement of these lenses L1 to L5 are set in consideration of the front cover 41 and the cover glass 56 of the imaging device 46.

The surface of the spherical object is designated by S1, the object side surface of the front cover 41 is designated by S2, the image side surface of the front cover 41 is designated by S3, the object side surface of the first lens L1 is designated by S4, the image side surface of the first lens L1 is designated by S5, the aperture diaphragm is designated by S6, the object side surface of the second lens L2 is designated by S7, the image side surface of the second lens L2 is designated by S8, the object side surface of the third lens L3 is designated by S9, the cemented surface of the third lens L3 and the fourth lens L4 is designated by S10, the image side surface of the fourth lens L4 is designated by S11, the object side surface of the fifth lens L5 is designated by S12, the image side surface of the fifth lens L5 is designated by S13, the object side surface of the cover glass 56 is designated by S14, and the image side surface of the cover glass 56 is designated by S15. These surfaces are each designated by the surface Si (surface number i=1 to 15). The imaging surface of the imaging device 46 coincides with the surface S15. The distance on the optical axis Z1 (on-axis surface separation) between the surface Si and the adjacent surface Si+1 on the image side is represented by Di (i=1 to 14).

As lens data of the imaging lens system 45c, the radii of curvature Ri of the surfaces Si, the on-axis surface separations Di, and the refractive indices Nd and the Abbe numbers νd of the front cover 41, the lenses L1 to L5, and the cover glass 56 at the d-line (wavelength 587.6 nm) are shown in Table 5. The F number, the focal length f, and the angle of view 2ω (degrees) of the imaging lens system 45c are also shown in a lower part of Table 5. This lens data (Table 5) of the imaging lens system 45c is lens data when normalization is performed so that the value of the focal length f becomes 1.0. The surfaces Si that are aspheric are marked with *.

The specific configurations of the aspheric surfaces are expressed by the same expression (2) as in Examples 1 and 2. For the aspheric surfaces Si, the conic constant K and the respective aspheric coefficients Ai are shown in Table 6.

TABLE 5

| | Surface number i | Ri | Di | $N_d$ | $v_d$ |
|---|---|---|---|---|---|
| (object) | 1 | 37.3880 | 24.3625 | | |
| | 2 | 13.0255 | 1.9297 | 1.57500 | 32.2 |
| | 3 | 11.0958 | 9.8032 | | |
| | 4* | 4.5962 | 1.2061 | 1.53039 | 55.2 |
| | 5* | 0.7626 | 1.8407 | | |
| (AD) | 6 | ∞ | 0.6628 | | |
| | 7* | 29.9508 | 1.9689 | 1.53039 | 55.2 |
| | 8* | −2.0294 | 0.2413 | | |
| | 9 | −29.3124 | 0.7236 | 1.92286 | 18.9 |
| | 10 | 4.8243 | 3.7077 | 1.72916 | 54.7 |
| | 11 | −5.0041 | 0.2412 | | |
| | 12* | 4.2899 | 2.4120 | 1.53039 | 55.2 |
| | 13* | −2.6662 | 0.4646 | | |
| (cover glass) | 14 | ∞ | 1.3146 | 1.55920 | 53.9 |
| | 15 | ∞ | 0.0000 | | |
| (imaging surface) | | ∞ | | | |

(AD: Aperture Diaphragm)
F Number 1.4
Focal length f 1.0
Angle of view 2ω (degree) 168.2

TABLE 6

| Surface number i | K | $A_3$ | $A_4$ | $A_5$ | $A_6$ |
|---|---|---|---|---|---|
| 4 | −1.0000 | −3.1911E−02 | −1.3237E−02 | 2.6667E−03 | 1.0090E−03 |
| 5 | −1.0000 | −7.2213E−01 | 1.0601E+00 | −3.2718E−01 | −4.1593E−01 |
| 7 | −1.0000 | 6.5178E−03 | −6.7047E−05 | −5.3129E−02 | 6.9474E−03 |
| 8 | −1.0000 | −3.8364E−03 | 1.5483E−02 | −1.0465E−02 | 1.2919E−03 |
| 12 | −1.0000 | −3.5805E−02 | 4.6875E−02 | −1.4934E−02 | −8.0459E−04 |
| 13 | −1.0000 | 7.1495E−02 | 1.7164E−03 | −8.3989E−04 | −1.0037E−03 |

| Surface number i | $A_7$ | $A_8$ | $A_9$ | $A_{10}$ | $A_{11}$ |
|---|---|---|---|---|---|
| 4 | 1.6604E−04 | −4.8482E−06 | −1.4417E−05 | −5.8184E−06 | −1.5724E−06 |
| 5 | −3.5206E−02 | 2.3279E−01 | 1.6234E−01 | −5.0788E−02 | −1.4257E−01 |
| 7 | 3.5489E−02 | −8.0267E−05 | −1.2559E−02 | −8.5493E−03 | 5.9519E−04 |
| 8 | −7.6095E−03 | 2.6037E−03 | 1.1487E−03 | 8.7078E−04 | 2.4020E−05 |
| 12 | 7.4194E−04 | 1.4060E−04 | −9.2904E−06 | −9.8806E−06 | −3.2675E−06 |
| 13 | −4.0258E−04 | −9.5516E−05 | 1.9474E−05 | 3.7285E−05 | 6.2802E−07 |

| Surface number i | $A_{12}$ | $A_{13}$ | $A_{14}$ | $A_{15}$ | $A_{16}$ |
|---|---|---|---|---|---|
| 4 | −1.6519E−07 | 7.8017E−08 | 5.7448E−08 | 1.9743E−08 | 1.3443E−09 |
| 5 | 5.1202E−02 | 1.3674E−02 | −5.5570E−03 | −5.0334E−05 | 1.6869E−17 |
| 7 | 1.6546E−02 | −1.0997E−02 | 1.7577E−03 | 1.2639E−04 | −1.4320E−07 |
| 8 | −8.3396E−04 | −1.2885E−04 | 2.9420E−04 | −2.4577E−05 | −1.2654E−05 |

TABLE 6-continued

| 12 | −7.1004E−07 | −3.9997E−08 | 3.3395E−08 | 2.5653E−08 | 1.1006E−08 |
| 13 | 3.3755E−07 | −1.8678E−07 | −1.3249E−07 | −4.0694E−08 | −8.1148E−09 |

| Surface number i | $A_{17}$ | $A_{18}$ | $A_{19}$ | $A_{20}$ |
| --- | --- | --- | --- | --- |
| 4 | −2.2787E−09 | −4.9358E−10 | 1.4347E−10 | 1.6018E−13 |
| 5 | 6.9935E−19 | −9.2841E−17 | −5.1143E−16 | −2.1203E−17 |
| 7 | 4.9356E−09 | 3.4281E−17 | 9.1722E−19 | 3.8025E−20 |
| 8 | −1.4738E−07 | 4.9787E−10 | 1.2020E−21 | 5.8918E−20 |
| 12 | 3.1808E−09 | −4.5905E−10 | −3.1571E−10 | −1.5121E−11 |
| 13 | 1.3025E−09 | 2.9595E−09 | −1.6047E−10 | −9.2263E−11 |

As shown in FIG. 12 and Tables 5 and 6, the first lens L1 has the shape and has the convex surface directed toward the object side, and the absolute value of the radius of curvature R4 of the object side surface S4 is larger than that of the radius of curvature R5 of the image side surface S5. That is, in the first lens L1, the curvature of the image side surface S5 is large as compared with that of the object side surface S4. The second lens L2 has the meniscus shape and has the convex surface directed toward the image side, and the absolute value of the radius of curvature R7 of the object side surface S7 is larger than that of the radius of curvature R8 of the image side surface S8. That is, in the second lens L2, the curvature of the image side surface S8 is large as compared with that of the object side surface S7.

Figure 13:
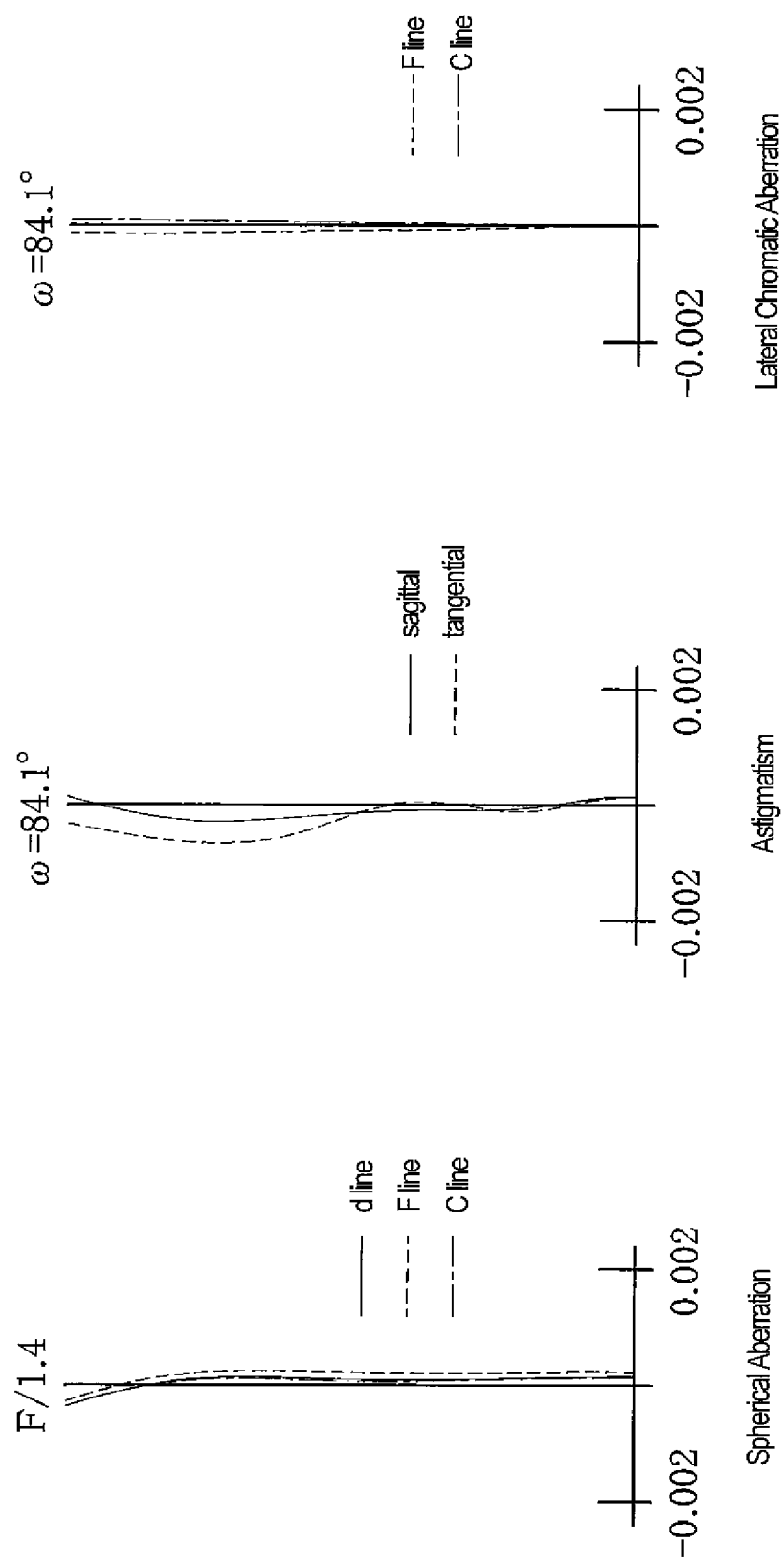
FIG. 13 shows graphic representations of aberrations of the imaging lens system of Example 3.

Further, the spherical aberrations, the astigmatisms, and the lateral chromatic aberrations of the imaging lens system 45c are shown in FIG. 13. These aberration diagraphs show aberrations when the front cover 41 and the cover glass 56 shown in Table 5 are provided. The way of representation of these aberrations is similar to that of Examples 1 and 2.

Figure 14:
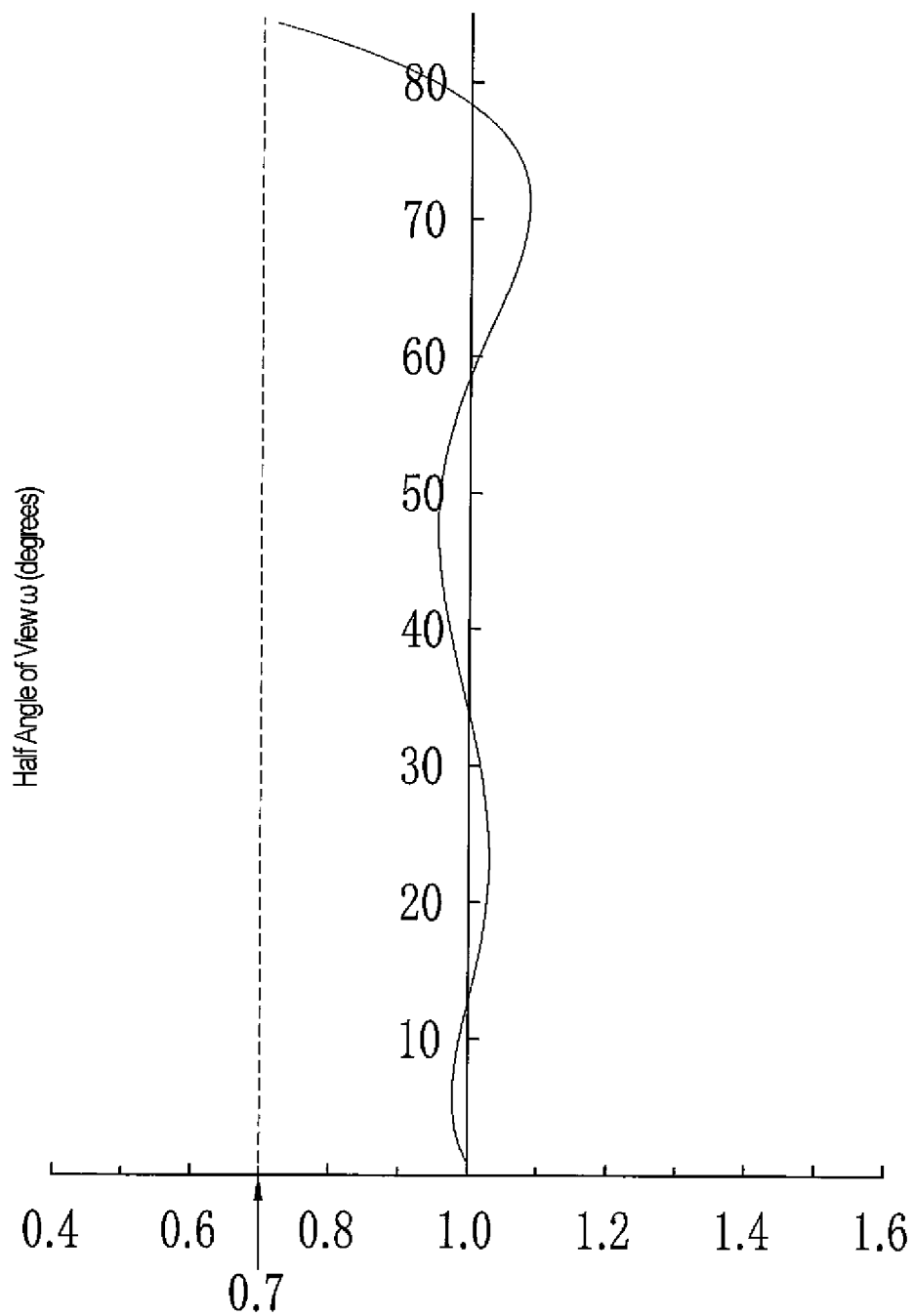
FIG. 14 is a graph showing distortion of the imaging lens system of Example 3.

As shown in FIG. 14, the imaging lens system 45c satisfies the conditional expression (1) with respect to a given angle of view ω, and the value of $$\frac{Y(\omega + \Delta\omega) - Y(\omega)}{Y(\Delta\omega)}$$

is larger than 0.7 in the entire range of the half angle of view ω of from 0 degree to 84.0 degrees and is close to 1.0 in the substantially entire angle of view. Therefore, in the images of spherical objects taken by the imaging lens system 45c, the image reduction and distortion are small even in the peripheral part. That is, although the imaging lens system 45c is a wide-angle lens whose maximum angle of view $2\omega_{MAX}$ is as large as 168.2 degrees, in images taken by this lens system, distortion that leads to lesion overlooking is not caused in the entire area including the peripheral part.

As described above, since the imaging lens system 45c includes five lenses, in particular, since the imaging lens system 45c has a two-group, five-lens configuration as mentioned above, distortion is excellently corrected in the entire range of the angle of view $2\omega_{MAX}$ without increase in size of the capsule endoscope. Further, in the imaging lens system 45c, not only distortion but also lateral chromatic aberration is excellently corrected in the entire area of the angle of view $2\omega_{MAX}$. Therefore, by mounting the imaging lens system 45c, a capsule endoscope can be obtained that is wide-angle and has its distortion and lateral chromatic aberration both excellently improved even in the peripheral part of the image while maintaining an easy-to-swallow size.

As described above, with the capsule endoscope of the embodiment of the invention, by providing the imaging lens system satisfying the conditional expression (1), a sufficient imaging area is maintained, and images in which there is little influence of distortion even in the peripheral part thereof can be obtained while an easy-to-swallow size of the capsule endoscope is maintained. Therefore, in spite of being a capsule endoscope whose posture in the patient's body is difficult to control, not only it can be prevented that images of some parts are not taken but also images can be obtained in which there is little possibility that lesions in the peripheral part of the taken image are overlooked at the time of diagnosis.

While the capsule endoscope whose posture and position in the patient's body are not controlled is described as an example in the above-described embodiment, the invention is not limited thereto. The invention is also suitably applicable to a capsule endoscope whose posture and position in the patient's body are controlled. The diagnosis method using the capsule endoscope shown in the above-described embodiment is merely an example, and the invention is not limited thereto.

What is claimed is:

1. An imaging lens system for a capsule endoscope, the imaging lens system configured to be disposed in a dome-shaped transparent cover, wherein
when a spherical object is imaged, the imaging lens system forms an image of an entire area from a center of the object to a maximum angle of view in a substantially same plane, and
the following conditional expression is satisfied with respect to an arbitrary half angle of view ω:

$0.7 < (Y(\omega+\Delta\omega) - Y(\omega))/Y(\Delta\omega)$ where Y(ω) denotes an image height for the half angle of view ω of the imaging lens system, and
Δω denotes an amount of minute change of the half angle of view (ω).

2. The imaging lens system according to claim 1, wherein the following conditional expression is satisfied:

$2\omega_{MAX} > 135$ degrees where $\omega_{MAX}$ denotes a maximum half angle of view.

3. A capsule endoscope comprising:
the imaging lens system according to claim 2.

4. A capsule endoscope comprising:
the imaging lens system according to claim 1.

5. The imaging lens system according to claim 1, comprising:
four lenses.

6. The imaging lens system according to claim 5, comprising, in order from an object side:
a first lens group having a negative refractive power;

a stop; and a second lens group having a positive refractive power.

7. The imaging lens system according to claim 6, wherein the following conditional expression is satisfied:

$$2\omega_{MAX} > 135 \text{ degrees}$$

where $\omega_{MAX}$ denotes a maximum half angle of view.

8. A capsule endoscope comprising:

the imaging lens system according to claim 7.

9. A capsule endoscope comprising:

the imaging lens system according to claim 6.

10. The imaging lens system according to claim 5, wherein the following conditional expression is satisfied:

$$2\omega_{MAX} > 135 \text{ degrees}$$

where $\omega_{MAX}$ denotes a maximum half angle of view.

11. A capsule endoscope comprising:

the imaging lens system according to claim 10.

12. A capsule endoscope comprising:

the imaging lens system according to claim 5.

13. The imaging lens system according to claim 1, comprising:

five lenses.

14. The imaging lens system according to claim 13 comprising, in order from an object side:

a first lens group having a negative refractive power;

a stop; and a second lens group having a positive refractive power.

15. The imaging lens system according to claim 14, wherein the following conditional expression is satisfied:

$$2\omega_{MAX} > 135 \text{ degrees}$$

where $\omega_{MAX}$ denotes a maximum half angle of view.

16. A capsule endoscope comprising:

the imaging lens system according to claim 15.

17. A capsule endoscope comprising:

the imaging lens system according to claim 14.

18. The imaging lens system according to claim 13, wherein the following conditional expression is satisfied:

$$2\omega_{MAX} > 135 \text{ degrees}$$

where $\omega_{MAX}$ denotes a maximum half angle of view.

19. A capsule endoscope comprising:

the imaging lens system according to claim 18.

20. A capsule endoscope comprising:

the imaging lens system according to claim 13.

* * * * *